(12) United States Patent
Matsuoka et al.

(10) Patent No.: US 10,753,870 B2
(45) Date of Patent: Aug. 25, 2020

(54) AUTOMATIC ANALYSIS APPARATUS INCLUDING A REACTION CONTAINER HOLDING PART HAVING A SURFACE THAT REFLECTS LIGHT EMITTED FROM A LIGHT SOURCE

(71) Applicant: Hitachi High-Tech Corporation, Minato-ku, Tokyo (JP)

(72) Inventors: Yuya Matsuoka, Tokyo (JP); Sakuichiro Adachi, Tokyo (JP); Akihisa Makino, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 0 days.

(21) Appl. No.: 16/328,818

(22) PCT Filed: Aug. 4, 2017

(86) PCT No.: PCT/JP2017/028354
§ 371 (c)(1),
(2) Date: Feb. 27, 2019

(87) PCT Pub. No.: WO2018/051671
PCT Pub. Date: Mar. 22, 2018

(65) Prior Publication Data
US 2019/0212262 A1 Jul. 11, 2019

(30) Foreign Application Priority Data

Sep. 14, 2016 (JP) .................................. 2016-179098

(51) Int. Cl.
*G01N 21/51* (2006.01)
*G01N 35/00* (2006.01)
(Continued)

(52) U.S. Cl.
CPC ............ *G01N 21/51* (2013.01); *G01J 1/0223* (2013.01); *G01J 1/0295* (2013.01); *G01J 1/10* (2013.01);
(Continued)

(58) Field of Classification Search
CPC ..... G01N 2021/4726; G01N 2021/473; G01N 2021/4764; G01N 2021/4769;
(Continued)

(56) References Cited

U.S. PATENT DOCUMENTS 4,552,458 A * 11/1985 Lowne ................. G01N 21/474
356/446
5,838,429 A * 11/1998 Hahn ................... G01N 21/255
356/39
(Continued)

FOREIGN PATENT DOCUMENTS

| JP | 2-221864 A | 9/1990 |
|----|------------|--------|
| JP | 2005-37242 A | 2/2005 |

(Continued)

OTHER PUBLICATIONS

International Search Report (PCT/ISA/210) issued in PCT Application No. PCT/JP2017/028354 dated Oct. 31, 2017 with English translation (four (4) pages).
(Continued)

*Primary Examiner* — Gordon J Stock, Jr.
(74) *Attorney, Agent, or Firm* — Crowell & Moring LLP

(57) ABSTRACT

This automatic analysis apparatus is provided with: an analysis port comprising a reaction container holding part that holds a reaction container storing the liquid mixture of a sample and a reagent, a light source that emits light to the liquid mixture stored in the reaction container held by the reaction container holding part, and a detector that detects light generated when the light from the light source is
(Continued)

emitted to the liquid mixture; and a control unit that controls the analysis port, and analyzes the sample on the basis of information about the detected light. The automatic analysis apparatus is characterized in that: the surface of an inner wall of the reaction container holding part is configured to reflect at least a portion of the light emitted from the light source; and the control unit executes control so as to emit the light from the light source in a state where the reaction container is not held by the reaction container holding part, to detect the light reflected on the surface of the inner wall of the reaction container holding part by the detector, and to not use the analysis port for analysis when the result of the detection shows that the detected light is less than a first value determined in advance.

20 Claims, 9 Drawing Sheets

(51) Int. Cl.
| | | |
|---|---|---|
| | *G01J 1/02* | (2006.01) |
| | *G01J 1/18* | (2006.01) |
| | *G01J 1/10* | (2006.01) |
| | *G01N 33/49* | (2006.01) |
| | *G01J 1/42* | (2006.01) |
| | *G01J 1/44* | (2006.01) |

(52) U.S. Cl.
CPC ............ *G01J 1/18* (2013.01); *G01N 33/4905* (2013.01); *G01N 35/00584* (2013.01); *G01N 35/00594* (2013.01); *G01J 2001/4247* (2013.01); *G01J 2001/444* (2013.01); *G01N 2021/513* (2013.01); *G01N 2201/0694* (2013.01); *G01N 2201/0695* (2013.01)

(58) Field of Classification Search
CPC ..... G01N 2021/4776; G01N 2021/513; G01N 2021/516; G01N 21/47; G01N 21/4738; G01N 21/49; G01N 21/51; G01N 21/4785; G01N 33/48; G01N 33/487; G01N 33/48778; G01N 33/50; G01N 33/49; G01N 33/4905; G01N 35/00; G01N 35/00584; G01N 35/00594; G01N 35/00613; G01N 35/00623; G01N 35/00693; G01N 2201/0694; G01N 2201/0695; G01J 1/0223; G01J 1/0271; G01J 1/0295; G01J 1/0437; G01J 1/044; G01J 1/0411; G01J 1/0466; G01J 1/10; G01J 1/124; G01J 1/18; G01J 2001/4247; G01J 2001/4252; G01J 2001/444

See application file for complete search history.

(56) References Cited

U.S. PATENT DOCUMENTS

| | | | | |
|---|---|---|---|---|
| 5,859,703 | A | * | 1/1999 | Aldridge ................ G01J 3/02 250/339.11 |
| 6,023,070 | A | * | 2/2000 | Wetegrove ........... G01N 21/532 250/573 |
| 9,182,344 | B1 | * | 11/2015 | Mitchell .............. G01N 21/534 |
| 9,400,247 | B2 | * | 7/2016 | Yamashita ............. G01N 33/49 |
| 9,664,678 | B2 | * | 5/2017 | Yogi .................... G01N 35/025 |
| 9,851,297 | B2 | * | 12/2017 | Battefeld ............... G01N 21/51 |
| 9,857,219 | B2 | * | 1/2018 | Nammoku ............ G01N 21/51 |
| 10,330,604 | B2 | * | 6/2019 | Konishi ................ G01N 21/77 |
| 2015/0147230 | A1 | | 5/2015 | Yoshikawa et al. |
| 2016/0245690 | A1 | | 8/2016 | Nammoku et al. |
| 2017/0212137 | A1 | | 7/2017 | Sasaki et al. |
| 2019/0195857 | A1 | * | 6/2019 | Iwasaki ................ G01N 33/49 |

FOREIGN PATENT DOCUMENTS

| | | |
|---|---|---|
| JP | 2009-168491 A | 7/2009 |
| JP | 2013-250218 A | 12/2013 |
| WO | WO 2015/029595 A1 | 3/2015 |
| WO | WO 2015/182256 A1 | 12/2015 |
| WO | WO 2016/006362 A1 | 1/2016 |

OTHER PUBLICATIONS

Japanese-language Written Opinion (PCT/ISA/237) issued in PCT Application No. PCT/JP2017/028354 dated Oct. 31, 2017 (six (6) pages).

* cited by examiner

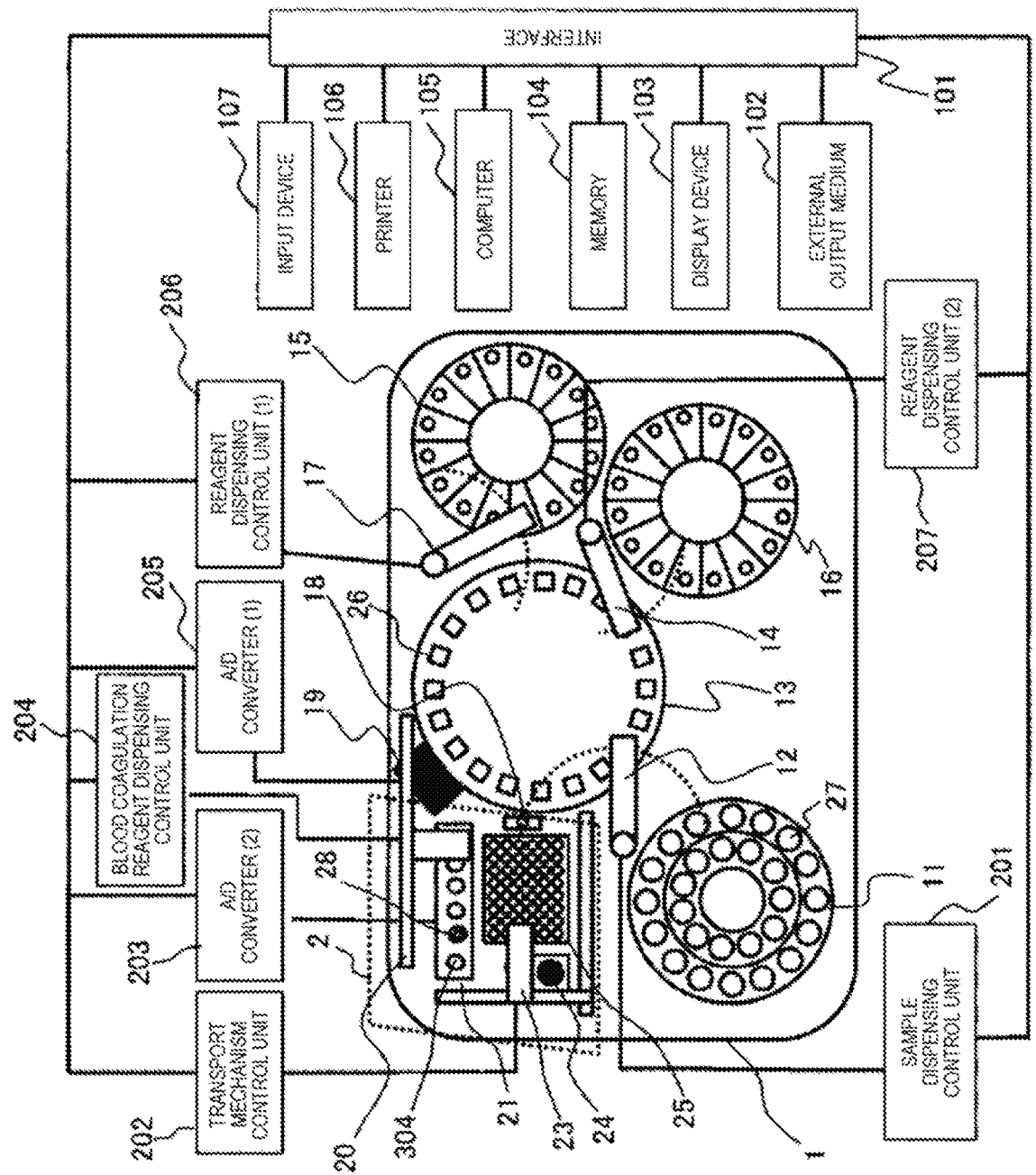
[FIG. 1]

FIG. 2A   TOP CROSS-SECTIONAL VIEW
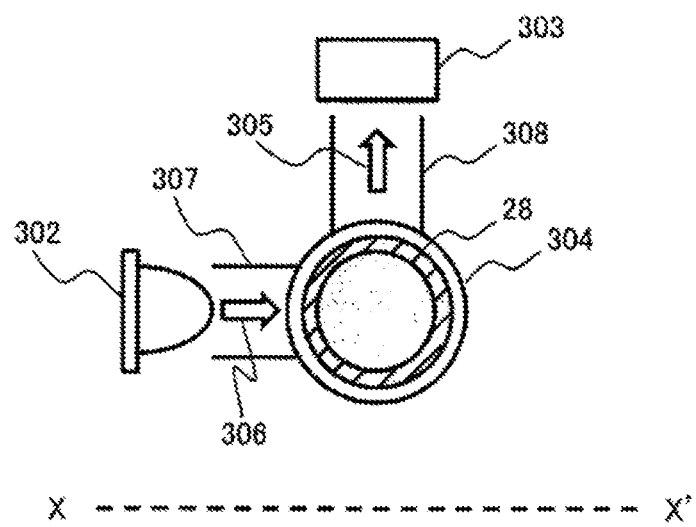
FIG. 2B   FRONT (X-X') CROSS-SECTIONAL VIEW
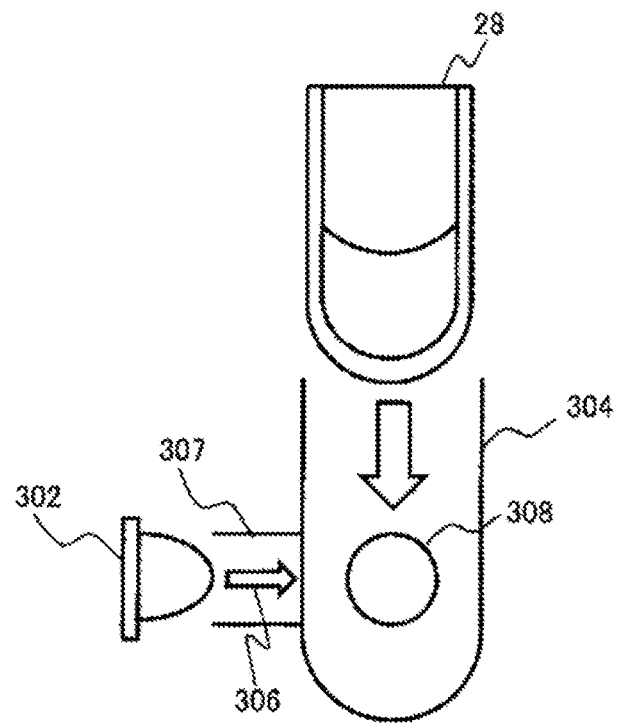

REACTION CONTAINER PRESENT

REACTION CONTAINER NOT PRESENT

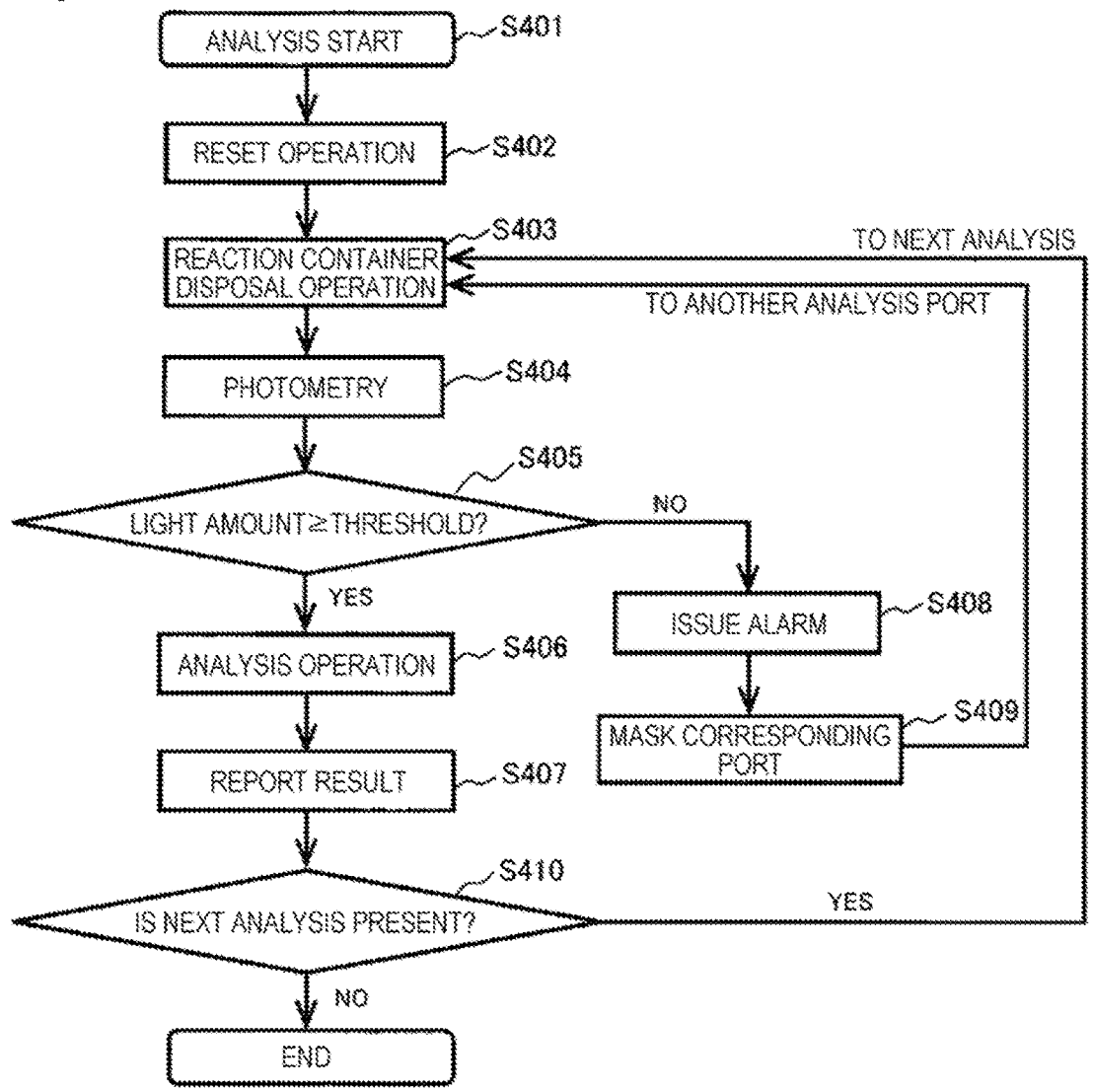
[FIG. 4]

REACTION CONTAINER PRESENT

REACTION CONTAINER NOT PRESENT

[FIG. 8]
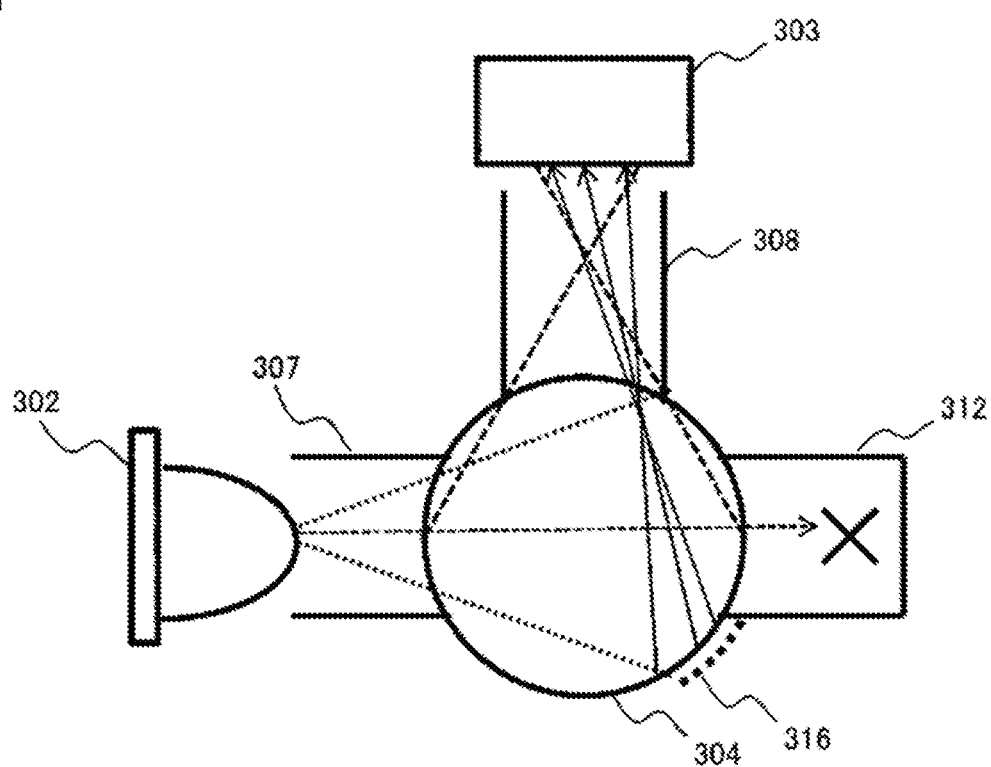

DURING ANALYSIS OPERATION (REACTION CONTAINER PRESENT)

DURING LIGHT AMOUNT CHECK (REACTION CONTAINER NOT PRESENT)

AUTOMATIC ANALYSIS APPARATUS INCLUDING A REACTION CONTAINER HOLDING PART HAVING A SURFACE THAT REFLECTS LIGHT EMITTED FROM A LIGHT SOURCE

TECHNICAL FIELD

The present invention relates to an automatic analysis apparatus that automatically analyzes a component included in a biological sample such as blood or urine, and particularly relates to an apparatus including an analysis port and a method using the apparatus, the analysis port including a light source that emits light to an analysis target and a detector that detects the light emitted from the light source.

BACKGROUND ART

As an apparatus that analyzes a component included in a sample such as blood, an automatic analysis apparatus that measures the amount of scattered light or transmitted light having a single or multiple wavelengths generated when light is emitted from a light source to a reaction solution, which is an analysis target, as a mixture of a sample and a reagent is known.

Examples of the automatic analysis apparatus include an apparatus for biochemical analysis that performs qualitative and quantitative analysis of a target component in a biological sample and an apparatus for blood coagulation analysis that measures coagulability of blood as a sample in the field of a biological examination or a hematological examination.

Here, in a case where a decrease in light amount caused by deterioration of the light source or incorporation of foreign matter into an optical path occurs, the reliability of analysis deteriorates such that a false result may be reported or the analysis may fail. Therefore, a biochemical automatic analysis apparatus including a reaction container that is cleaned to be repeatedly used has a function of cleaning the reaction container before a start of analysis, performing photometry (blank measurement) of transmitted light or scattered light in a state where only water is put into the cleaned reaction container, comparing the measurement result and a reference value to each other to detect scratches or contamination of the reaction container or incorporation of foreign matter into an optical path, and notifying an operator not to use the reaction container in a case where the reaction container is abnormal.

On the other hand, in an automatic analysis apparatus that performs analysis such as blood coagulation analysis of measuring scattered light using a disposable reaction container, light is not incident on a detector in a state where a reaction container and a reaction solution are not present. Therefore, blank measurement cannot be performed per analysis operation. Accordingly, in order to check a deterioration state of a light source or incorporation of foreign matter on an optical path, regularly or in a case where an abnormal analysis result occurs, the amount of light incident on the detector is measured by providing a standard material called a standard solution or a standard scatterer.

In an automatic analysis apparatus described in PTL 1 in which a light source is arranged below a disposable reaction container to measure scattered light, a light detector is provided in a transport mechanism of the reaction container to measure the amount of light emitted from the light source. In this configuration, deterioration of the light source or foreign matter in an analysis port can be detected by measuring the light amount under either condition irrespective of whether or not the reaction container is held by the transport mechanism.

CITATION LIST

Patent Literature

PTL 1: JP-A-2013-250218

SUMMARY OF INVENTION

Technical Problem

In a clinical examination, the accuracy of an analysis result and the reliability of an apparatus are required. In particular, blood coagulation analysis that measures coagulability of blood is mainly used in an urgent situation, for example, before a surgery. Therefore, it is necessary to immediately report a highly reliable analysis result. In particular, for an urgent sample, the time from sample loading to result reporting is extremely important, and it is necessary to minimize delay of result reporting caused by problems of the apparatus.

According to the method described in PTL 1, by checking the light amount per start of analysis, the risk of false analysis result or reporting delay caused by deterioration of a light source or incorporation of foreign matter into an optical path can be reduced.

However, in this technique, it is necessary that the detector for checking deterioration of the light source or foreign matter in an analysis port is provided in the transport mechanism of the reaction container separately from a detector used for analysis. Therefore, the size of the transport mechanism increases, which increases the costs. In addition, an arrangement direction of the detector for checking the light source and an arrangement direction of the detector for analysis are different from each other. Therefore, the detector itself for analysis and foreign matter on an optical path in the direction in which the detector for analysis is arranged cannot be detected. Further, in a case where the light amount is measured in a state where the transport mechanism does not hold the reaction container in order to exclude an individual difference between reaction containers, it is necessary to add an irregular operation that is not necessary for typical analysis, which leads to a decrease in the processing capacity of the apparatus.

Solution to Problem

According to one aspect for solving the problems, there are provided an automatic analysis apparatus and a method using the apparatus. The automatic analysis apparatus including: an analysis port including a reaction container holding part that holds a reaction container storing a liquid mixture of a sample and a reagent, a light source that emits light to the liquid mixture stored in the reaction container held by the reaction container holding part, and a detector that detects light generated when the light is emitted from the light source to the liquid mixture; and a control unit that controls the analysis port, in which the sample is analyzed based on information on the detected light, a surface of the reaction container holding part is configured to reflect at least a part of the light emitted from the light source, and the control unit executes control so as to emit the light from the light source in a state where the reaction container is not held by the reaction container holding part, to detect the light reflected on the surface of the reaction container holding part by the detector, and not to use the analysis port for analysis when the result of the detection shows that the detected light is less than a first value determined in advance.

Advantageous Effects of Invention

According to the aspect, an additional mechanism such as a detector or an additional mechanism operation that is not necessary for typical analysis is not required, deterioration of a light source and foreign matter on all the optical paths that are required to be checked including a direction in which a detector used for analysis is arranged can be detected, and an analysis result having high accuracy and reliability can be provided even in an urgent situation.

BRIEF DESCRIPTION OF DRAWINGS

FIG. 1 is a diagram illustrating a basic configuration of an automatic analysis apparatus according to an embodiment.

FIGS. 2A and 2B are diagrams illustrating a basic configuration of a blood coagulation time detecting unit in the automatic analysis apparatus according to the embodiment.

FIG. 4 is a flowchart illustrating an example of a light amount check operation according to the embodiment (Example 1).

FIG. 8 is a diagram (top view) illustrating an optical configuration of the blood coagulation time detecting unit according to the embodiment (Example 9).

DESCRIPTION OF EMBODIMENTS

Figure 3A:
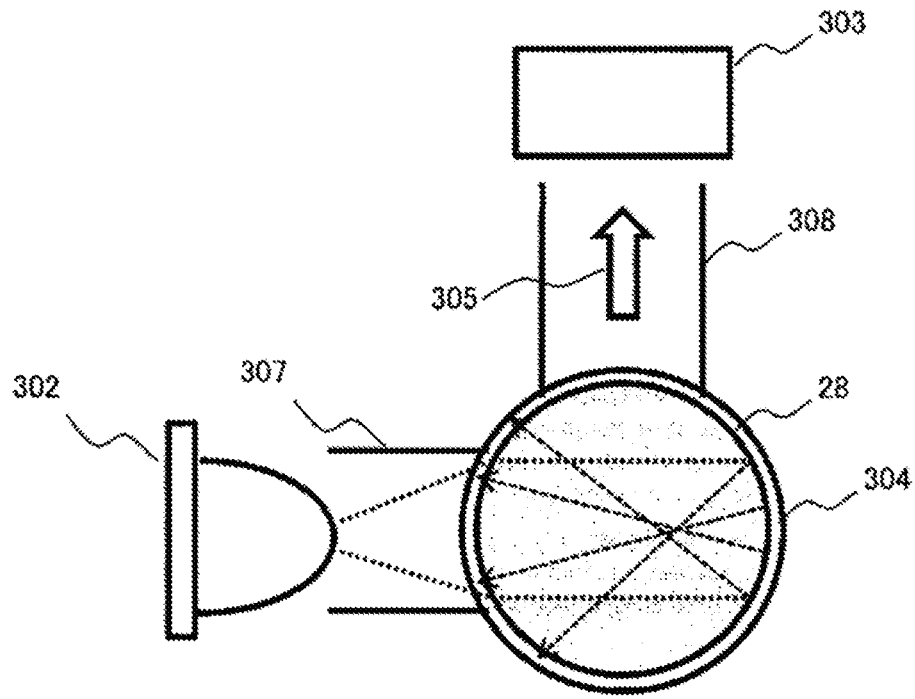
FIGS. 3A and 3B are diagrams (top view) illustrating an optical configuration of the blood coagulation time detecting unit according to the embodiment (Example 1).

Hereinafter, an embodiment of the present invention will be described with reference to the drawings. In all the drawings, components having the same functions are represented by the same reference numerals in principle, and description thereof will not be repeated.

Example 1

<Basic Configuration of Apparatus>

FIG. 1 is a diagram illustrating a basic configuration of an automatic analysis apparatus according to the embodiment. Here, as an aspect of the automatic analysis apparatus, a composite type automatic analysis apparatus including a turntable type biochemical analyzing unit and a blood coagulation time analyzing unit will be described.

As illustrated in the drawing, in an automatic analysis apparatus 1, a reaction disk 13, a sample disk 11, a first reagent disk 15, a second reagent disk 16, a blood coagulation time analyzing unit 2, a photometer 19 are arranged on a housing.

The reaction disk 13 is a disk-shaped unit that is rotatable clockwise and counterclockwise, in which plural reaction containers (for biochemical analysis) 26 can be arranged on a circumference thereof.

The sample disk 11 is a disk-shaped unit that is rotatable clockwise and counterclockwise, in which plural sample container 27 each of which stores a sample such as a standard sample or a test sample can be arranged on a circumference thereof.

The first reagent disk 15 and the second reagent disk 16 are disk-shaped units that are rotatable clockwise and counterclockwise, in which plural reagent containers each of which stores a reagent including a component that is reactive with a component of each examination item included in the sample can be arranged on a circumference thereof. In addition, although not illustrated in the drawing, the first reagent disk 15 and the second reagent disk 16 may include a cooling mechanism or the like such that the reagent in the arranged reagent container can be cooled.

A sample dispensing probe 12 is arranged between the sample disk 11 and the reaction disk 13. Due to a rotation operation of the sample dispensing probe 12, an operation of aspirating and dispensing the sample can be performed on the sample container 27 on the sample disk 11, the reaction container (for biochemical analysis) 26 on the reaction disk 13, and a reaction container (for blood coagulation analysis) 28 at a sample dispensing position 18 of the blood coagulation time analyzing unit 2.

Likewise, a first reagent dispensing probe 17 is arranged between the first reagent disk 16 and the reaction disk 13, and a second reagent dispensing probe 14 is arranged between the second reagent disk 15 and the reaction disk 13. Due to respective rotation operations of the first reagent dispensing probe 17 and the second reagent dispensing probe 14, a dispensing operation such as aspiration or discharge can be performed on the reaction container (for biochemical analysis) 26 on the reaction disk 13 and the reagent containers on the first reagent disk 15 and the second reagent disk 16.

The blood coagulation time analyzing unit 2 mainly includes a blood coagulation time detecting unit 21, a blood coagulation reagent dispensing probe 20, a reaction container magazine 25, the sample dispensing position 18, a reaction container transport mechanism 23, and a reaction container disposal hole 24.

Next, a control system and a signal processing system relating to the automatic analysis apparatus 1 will be simply described. A computer 105 is connected to a sample dispensing control unit 201, a reagent dispensing control unit (1) 206, a reagent dispensing control unit (2) 207, a blood coagulation reagent dispensing control unit 204, an A/D converter (1) 205, an A/D converter (2) 203, and a transport mechanism control unit 202 through an interface 101 and transmits a signal as an instruction to each of the control units.

The sample dispensing control unit 201 controls the sample dispensing operation of the sample dispensing probe 12 based on an instruction received from the computer 105.

In addition, the reagent dispensing control unit (1) 206 and the reagent dispensing control unit (2) 207 controls the reagent dispensing operation of the first reagent dispensing probe 17 and the second reagent dispensing probe 14 based on an instruction received from the computer 105.

In addition, the transport mechanism control unit 202 controls the operation of the reaction container transport mechanism 23 transporting the disposable reaction container (for blood coagulation analysis) 28 between the reaction container magazine 25, the sample dispensing position 18, an analysis port 304 of the blood coagulation time detecting unit 21, and the reaction container disposal hole 24 on a basis of an instruction received from the computer 105.

In addition, the blood coagulation reagent dispensing control unit 204 causes the blood coagulation reagent dispensing probe 20 to dispense a reagent for blood coagulation into the reaction container (for blood coagulation analysis) 28 storing the sample that is dispensed by the sample dispensing probe 12 and held by a reaction container holding part of the analysis port 304 based on an instruction received from the computer 105. Alternatively, the blood coagulation reagent dispensing control unit 204 causes the blood coagulation reagent dispensing probe 20 to dispense a pre-treatment solution into the empty reaction container (for blood coagulation analysis) 28, the pre-treatment solution being a liquid mixture that is obtained by mixing the sample and a first reagent for blood coagulation analysis with each other in the reaction container (for biochemical analysis) 26. In this case, subsequently, the blood coagulation reagent dispensing control unit 204 causes the blood coagulation reagent dispensing probe 20 to dispense a second reagent for blood coagulation analysis into the reaction container 28 storing the pre-treatment solution. Here, the reagents for blood coagulation analysis are arranged in the first reagent disk 15 and the second reagent disk 16 and are used for blood coagulation analysis after being temporarily dispensed into the reaction container (for biochemical analysis) 26 on the reaction disk 13 by the first reagent dispensing probe 17 and the second reagent dispensing probe 18 as necessary.

A photometric value of transmitted light or scattered light in the reaction solution of the reaction container (for biochemical analysis) 26 that is converted into a digital signal by the A/D converter (1) 205 and a photometric value of transmitted light or scattered light in the reaction solution of the disposable reaction container (for blood coagulation analysis) 28 that is converted into a digital signal by the A/D converter (2) 203 are input to the computer 105.

A printer 106 for printing a measurement result as a report or the like, a memory 104 as a storage device, an external output medium 102, an input device 107 such as a keyboard for inputting an operation instruction or the like, and a display device 103 for displaying a screen are connected to the interface 101. Examples of the display device 103 include a liquid crystal display and a CRT display.

Analysis of a biochemical analytical item by the automatic analysis apparatus 1 is performed according to the following procedure. First, an operator requests an examination item for each sample using the input device 107 such as a keyboard. In order to analyze the sample for the requested examination item, the sample dispensing probe 12 dispenses a predetermined amount of the sample from the sample container 27 into the reaction container (for biochemical analysis) 26 according to analysis parameters.

The reaction container (for biochemical analysis) 26 into which the sample is dispensed is transported by the rotation of the reaction disk 13 and stops at a reagent receiving position. A pipette nozzle of each of the first reagent dispensing probe 17 and the second reagent dispensing probe 14 dispenses a predetermined amount of reagent solution into the reaction container (for biochemical analysis) 26 according to analysis parameters of the corresponding examination item. Regarding the dispensing order of the sample and the reagent, the reagent may be dispensed before the sample contrary to the example.

Next, the sample and the reagent are stirred and mixed using a stirring mechanism (not illustrated). When the reaction container (for biochemical analysis) 26 passes through a photometric position, photometry of transmitted light or scattered light of the reaction solution as the liquid mixture of the sample and the reagent stored in the reaction container (for biochemical analysis) 26 is performed by the photometer 19. The transmitted light or the scattered light having undergone photometry is converted into numeric data in proportion to the light amount by the A/D converter (1) 205, and the numeric data is input to the computer 105 through the interface 101.

Concentration data is calculated based on a calibration curve estimated in advance using the converted numerical value with an analysis method designated per examination item. The component concentration data as the analysis result of each examination item is output to the printer 106 or the screen of the display device 103.

Before performing the above-described measuring operation, the operator sets various parameters required for analysis or registers the reagent and the sample through the operation screen of the display device 103. In addition, after the measurement, the operator checks the analysis result through the operation screen on the display device 103.

In addition, analysis of a blood coagulation time item by the automatic analysis apparatus 1 is performed according to the following procedure.

First, the operator requests an examination item for each sample using the input device 107 such as a keyboard. In order to analyze the sample for the requested examination item, the reaction container transport mechanism 23 transports the disposable reaction container (for blood coagulation analysis) 28 from the reaction container magazine 25 to the sample dispensing position 18. The sample dispensing probe 12 dispenses a predetermined amount of the sample from the sample container 27 into the reaction container (for blood coagulation analysis) 28 according to analysis parameters.

The reaction container (for blood coagulation analysis) 28 into which the sample is dispensed is transported to the analysis port 304 of the blood coagulation time detecting unit 21 by the reaction container transport mechanism 23 and is heated to a predetermined temperature. The first reagent dispensing probe 17 dispenses a predetermined amount of reagent solution into the reaction container (for biochemical analysis) 26 on the reaction disk 13 according to analysis parameters of the corresponding examination item. In the reaction disk 13, a thermostat (not illustrated) is provided. Therefore, the reagent solution dispensed into the reaction container (biochemical analysis) 26 is heated to 37° C.

Next, the blood coagulation reagent dispensing probe 20 aspirates the reagent dispensed into the reaction cell (for biochemical analysis) 26, the reagent is heated to a predetermined temperature by a heating mechanism (not illustrated) in the blood coagulation reagent dispensing probe 20, and the heated reagent is discharged into the reaction container (for blood coagulation analysis) 28.

When the reagent is discharged, photometry of transmitted light or scattered light of light emitted to the reaction container (for blood coagulation analysis) 28 starts. The transmitted light or the scattered light having undergone photometry is converted into numeric data in proportion to the light amount by the A/D converter (2) 203, and the numeric data is input to the computer 105 through the interface 101.

The time required for blood coagulation reaction (hereinafter, also simply referred to as "blood coagulation time") is obtained using the converted numerical value. For example, regarding an examination item such as ATPP (activated partial thromboplastin time), the blood coagulation time obtained as described above is output as the analysis result. Here, regarding an examination item such as Fbg (fibrinogen), component concentration data is further obtained with respect to the obtained blood coagulation time based on a calibration curve estimated in advance with an analysis method designated per examination item and is output as the analysis result. The blood coagulation time or the component concentration data as the analysis result of each examination item is output to the printer 106 or the screen of the display device 103.

Here, before performing the above-described measuring operation, the operator sets various parameters required for analysis or registers the reagent and the sample in advance through the operation screen of the display device 103. In addition, the operator can check the analysis result after the measurement through the operation screen on the display device 103.

In addition, the place into which the sample is discharged by the sample dispensing probe 12 may be the reaction container (for biochemical analysis) 26. In this case, after causing the sample to react with the pre-treatment solution in advance in the reaction container (for biochemical analysis) 26, the sample can be dispensed into the reaction container (for blood coagulation analysis) 28 by the sample dispensing probe 12.

In the blood coagulation reagent dispensing probe 20, stirring called discharge stirring is performed, the discharge stirring being a method of mixing the reagent with the sample in the reaction container (for blood coagulation analysis) 28 using a force with which the reagent is discharged to the sample stored in the reaction container (for blood coagulation analysis) 28 in advance. Regarding the dispensing order of the sample and the reagent, the reagent may be dispensed before the sample contrary to the example. In this case, the sample may be mixed with the reagent using a force with which the sample is discharged.

Next, a structure of the blood coagulation time detecting unit 21 will be described. Although described in detail below using FIG. 2, the blood coagulation time detecting unit 21 includes a light source 302 and a scattered light detector 303 in one or plural analysis ports 304 where the disposable reaction container (for blood coagulation analysis) 28 can be loaded, and the blood coagulation time detecting unit 21 can detect an intensity of scattered light of light emitted to the reaction solution in the reaction container (for blood coagulation analysis) 28.

In FIG. 1, the blood coagulation reagent dispensing probe 20 performs the aspirating operation of the reagent stored in the reaction container (for biochemical analysis) 26 on the reaction disk 13 and the dispensing operation of the reagent to the disposable reaction container (for blood coagulation analysis) 28 loaded into the blood coagulation time detecting unit 21 by the reaction container transport mechanism 23. The reaction container magazine 25 is used for aligning and loading the plural disposable reaction containers (for blood coagulation analysis) 28. The sample dispensing position 18 is provided for dispensing the sample as the analysis target loaded on the sample disk 11 into the reaction container (for blood coagulation analysis) 28. Here, the reaction container (for blood coagulation analysis) 28 is transported from the reaction container magazine 25 by the reaction container transport mechanism 23.

Here, FIG. 2 is a diagram illustrating a basic configuration of the blood coagulation time detecting unit in the automatic analysis apparatus according to the embodiment, that is, a diagram illustrating an arrangement configuration of the reaction container, the light source, and the detector in the analysis port.

FIG. 2(a) is a cross-sectional view illustrating the arrangement configuration of the light source and the detector when seen from the top, and FIG. 2(b) is a cross-sectional view illustrating the same arrangement configuration when seen from the front (taken along line X-X' of FIG. 2(a)). Here, the blood coagulation time detecting unit 21 in FIG. 1 includes the light source 302 and the scattered light detector 303 as described above and further includes one or plural analysis ports 304 including a reaction container holding part where the disposable reaction container (for blood coagulation analysis) 28 can be provided from the top. In addition, in this configuration, the detector 303 is arranged on a side surface of the reaction container (for blood coagulation analysis) 28 such that scattered light of the light emitted from the light source 302 to the reaction solution in the reaction container (for blood coagulation analysis) 28 can be detected. An emission slit 307 that adjusts an emission range of the light emitted from the light source 302 is provided between the light source 302 and the reaction container (for blood coagulation analysis) 28, and a light receiving slit 308 that adjusts a range of light detected by the scattered light detector 303 is provided between the reaction container (for blood coagulation analysis 28) and the scattered light detector 303.

<Method of Checking Light Amount Using Photometry of Light Reflected on Analysis Port Wall Surface>

Figure 3B:
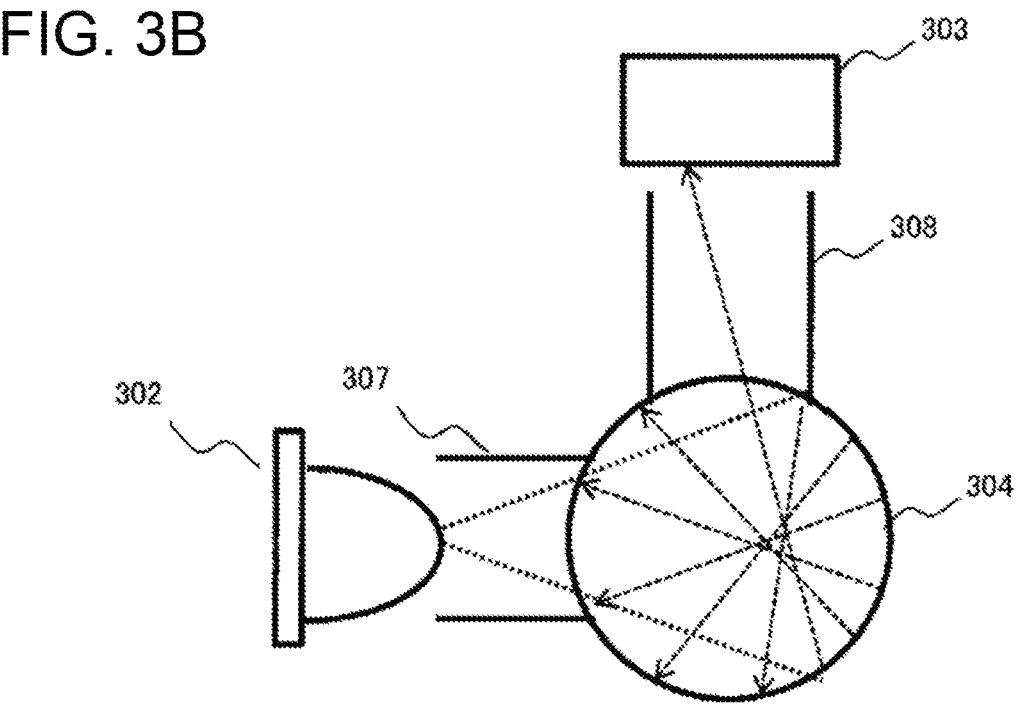

FIG. 3 illustrates an example of an optical configuration of the blood coagulation time detecting unit according to the embodiment. FIG. 3(a) illustrates light rays in a case where the reaction container (for blood coagulation analysis) 28 is provided in the reaction container holding part of the analysis port 304. The light emitted from the light source 302 is refracted when incident on the reaction container (for blood coagulation analysis) 28, a part of the emitted light is scattered, and another part of the emitted light is transmitted. At this time, scattered light 305 is incident on the scattered light detector 303. Light that is not incident on the scattered light detector 303 collides with an inner wall surface of the analysis port 304 that is surface-treated to slightly reflect light, is reflected and absorbed, and is attenuated. FIG. 3(b) illustrates light rays in a case where the reaction container (for blood coagulation analysis) 28 is not provided in the reaction container holding part of the analysis port 304. As illustrated in the drawing, in a case where the reaction container (for blood coagulation analysis) 28 is not provided, the above-described light refraction does not occur. Therefore, the light emitted from the light source 302 is widely spread and emitted to the wall surface of the reaction container holding part of the analysis port 304. At this time, the part of the light that is slightly reflected on the wall surface is incident on the scattered light detector 303.

Accordingly, under the condition that a reflectance of the wall surface is constant all the time, by measuring the output of the scattered light detector 303, that is, the light amount in a state where the reaction container (for blood coagulation analysis) 28 is not provided in the reaction container holding part of the analysis port 304, the intensity of the light emitted from the light source 302 can be measured more actively as compared to a state where the reaction container (for blood coagulation analysis) 28 is provided in the reaction container holding part of the analysis port 304. When the result of the measurement shows that the light amount is less than a reference (first value) determined in advance, it is presumed that deterioration of the light source 302 or incorporation of foreign matter into an optical path occurs. On the other hand, when the result of the measurement shows that the light amount is more than a reference (second value) that is a higher value than the first value, it is presumed that deterioration of the surface treatment or wear of the analysis port 304 occurs.

FIG. 4 is a flowchart illustrating an example of a light amount check operation according to the embodiment. Using FIG. 4, the light amount check operation in the above-described configuration and a method of masking the analysis port based on the light amount check operation will be described.

First, the start of an analysis operation is instructed in Step S401 (S401). Next, the apparatus performs an operation of resetting the respective mechanisms (S402) and then performs an operation of disposing the reaction container used for the previous analysis (S403).

Next, in a state where the light source 302 is turned on and the reaction container (for blood coagulation analysis) 28 is not provided in the reaction container holding part of the analysis port 304, photometry of the scattered light detector 303 is performed (S404). Whether or not the light amount is more than a threshold as a preset reference is determined based on the result of the photometry (S405). The threshold can be set to be one value or can be set to be a width of a predetermined range as described above, that is, to be in a range from the first reference value as the lower value side to the second reference value as the higher value side. In this flowchart, a case where the first reference value is set as the threshold will be described below.

Returning to FIG. 4, when the result of the determination shows that the light amount is more than or equal to the threshold, the analysis port 304 is used, the reaction container (for blood coagulation analysis) 28 is provided in the reaction container holding part, and the analysis operation is performed on the reaction solution that is the liquid mixture of the sample and the reagent dispensed into the reaction container (for blood coagulation analysis) 28 (S406). After the analysis ends, the result is reported (S407), and whether or not the next analysis is present is determined (S410). Here, when the next analysis is present, the process returns to Step S403, and the steps after the reaction container disposal operation (S403) are repeated.

On the other hand, when the light amount is less than the threshold in Step S405, as described above, it is presumed that deterioration of the light source 302 or incorporation of foreign matter into an optical path in the analysis port 304 occurs. An alarm is issued to give a notification to the operator (S408), a control is performed such that the corresponding analysis port 304 is masked not to be used (S409), and the operations after Step S403 are performed using another analysis port 304.

As a result, whether or not the analysis port 304 is in a normal state can be determined per execution of analysis. Therefore, the risk that the analysis result is false or the risk that reporting is delayed by re-examination or urgent maintenance can be reduced.

In the above-described configuration, the light amount may be checked not only per analysis operation but also at any timing such as a timing at which the apparatus starts, a timing at which a maintenance item is manually performed, or a timing at which an operation starts. In addition, the timing at which the light amount is checked may be set by the user. The timing can be set, for example, by the user inputting and selecting the timing through condition setting means such as the input device 107 while checking the display contents on the display device 103.

Example 2

In this example, in addition to the functions of Example 1, a function of storing light amount data acquired per analysis operation in the memory 104 such that a progress state of time-dependent deterioration of the light source 302 from the initial state can be displayed and checked by the display device 103 in a chronological manner is provided. Since a user or a service person can check the state, the light source 302 can be replaced before exerting an influence on analysis. As a result, before a part of the analysis ports 304 are masked such that the processing capacity decreases, the replacement or maintenance of the light source 302 can be performed as a preventive treatment, and the reliability of examination work can be improved.

Example 3

In a second embodiment, a function of urging the user to replace the light source 302 by estimating a period during which the light amount of the light source 302 is less than the threshold (first value) as the lower value side in the width of the predetermined range as the above-described reference based on a progress state of time-dependent deterioration of the light source 302 from the initial state and an operational state of the apparatus is provided.

As a result, before a part of the analysis ports 304 are masked such that the processing capacity decreases, the maintenance can be reliably performed, and the reliability of examination work can be improved. In addition, the frequency at which the service person checks the light amount can be reduced, which contributes to a reduction in costs and a reduction in apparatus stop time.

Example 4

In Example 1, depending on the kind of the light source 302 to be used, a long period of time may be required until the light source 302 is stable after being turned on. In this case, when analysis is performed before the light source 302 becomes stable, the reliability of the analysis result deteriorates. Therefore, a function of continuously measuring the light amount after turning on the light source to determine whether or not the light source 302 is stable and controlling an analysis operation not to be performed until the light source becomes stable can be provided.

As a result, deterioration in the reliability of the analysis result caused by performing analysis before the light source 302 becomes stable can be prevented, and the light source 302 can be used at an appropriate timing, that is, immediately after being stable by actually determining whether or not the light source 302 is stable. Accordingly, the time can be reduced as compared to a case where analysis starts after providing a surplus time such that the light source 302 becomes sufficiently stable.

Example 5

In Example 1, the result of checking the light amount per analysis may be stored in the memory 104 together with the previous result data. In this configuration, for example, in a case where the current value is different from the previous value by more than a predetermined range, it is determined that foreign matter may be incorporated into an optical path, and a control is performed to mask the analysis port 304 so as not to use the analysis port 304. In addition, in a case where the apparatus includes plural analysis ports 304, the analysis operation is performed using another analysis port 304. Here, the predetermined range is provided separately from the first and second reference values and is determined based on the difference between the current value and the previous value.

Example 6

FIG. 5 illustrates an example of an optical configuration of the blood coagulation time detecting unit according to the embodiment and illustrates an optical configuration of an automatic analysis apparatus in which a transmitted light detector 309 that detects transmitted light is further provided in addition to the disposable reaction container (for blood coagulation analysis) 28 and the scattered light detector 303 that detects scattered light in FIG. 2.

Figure 5A:
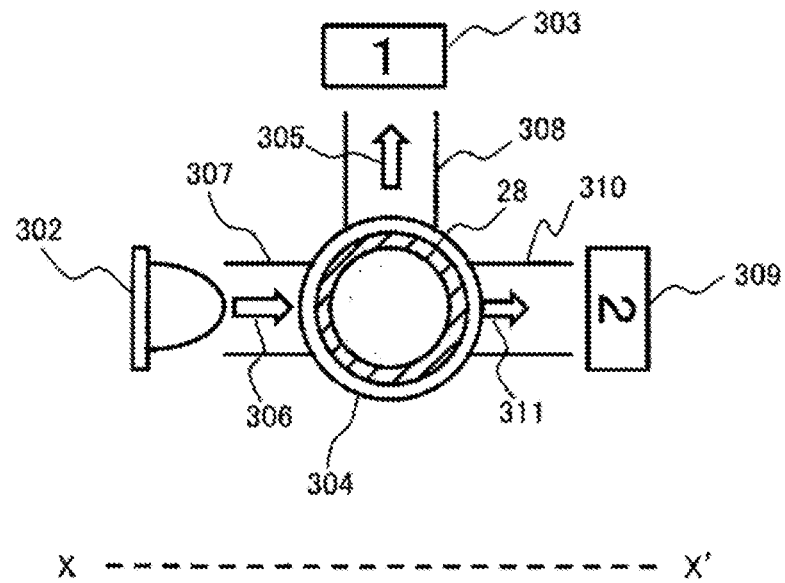
FIGS. 5A and 5B are diagrams illustrating an optical configuration of the blood coagulation time detecting unit according to the embodiment (Example 6).
Figure 5B:
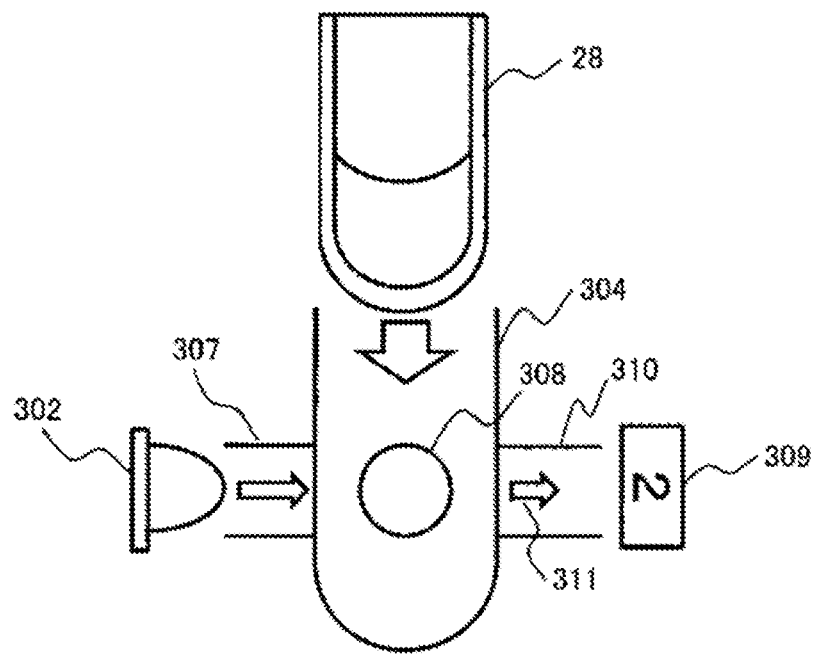

FIG. 5(a) is a cross-sectional view illustrating the arrangement configuration of the light source and the detector when seen from the top, and FIG. 5(b) is a cross-sectional view illustrating the same arrangement configuration when seen from the front (taken along line X-X' of FIG. 5(a)). The transmitted light detector 309 is arranged opposite to the light source 302 (opposite to the light source 302 with respect to the reaction container holding part of the analysis port 304), and the scattered light detector 303 is arranged at a position where scattered light of the light emitted from the light source 302 to the reaction solution in the reaction container (for blood coagulation analysis) 28 can be detected, for example, at a position that is shifted from the transmitted light detector 309 by about 90° as illustrated in the drawing. In addition, a transmitted light slit 310 that adjusts a range of light transmitted through the reaction container (for blood coagulation analysis) 28 is provided between the reaction container (for blood coagulation analysis) 28 and the transmitted light detector 309.

Although the operation sequence is the same as described above using FIG. 4, both the scattered light detector 303 and the transmitted light detector 309 are used in the photometry operation (S404) for checking the light amount, and any one of the scattered light detector 303 or the transmitted light detector 309 is used in the analysis operation (S406). Deterioration of the light source 302 or incorporation of foreign matter into an optical path can be detected using any one of the detectors. However, when the transmitted light detector 309 is used, deterioration of the light source 302 or incorporation of foreign matter into an optical path can be detected without an influence on the surface of the analysis port 304. Therefore, the determination can be performed with higher accuracy and higher sensitivity.

On the other hand, in a configuration in which the scattered light detector 303 is used, when the light amount is more than the threshold, deterioration of the surface treatment or wear of the analysis port 304 can also be detected.

Example 7

Figure 6A:
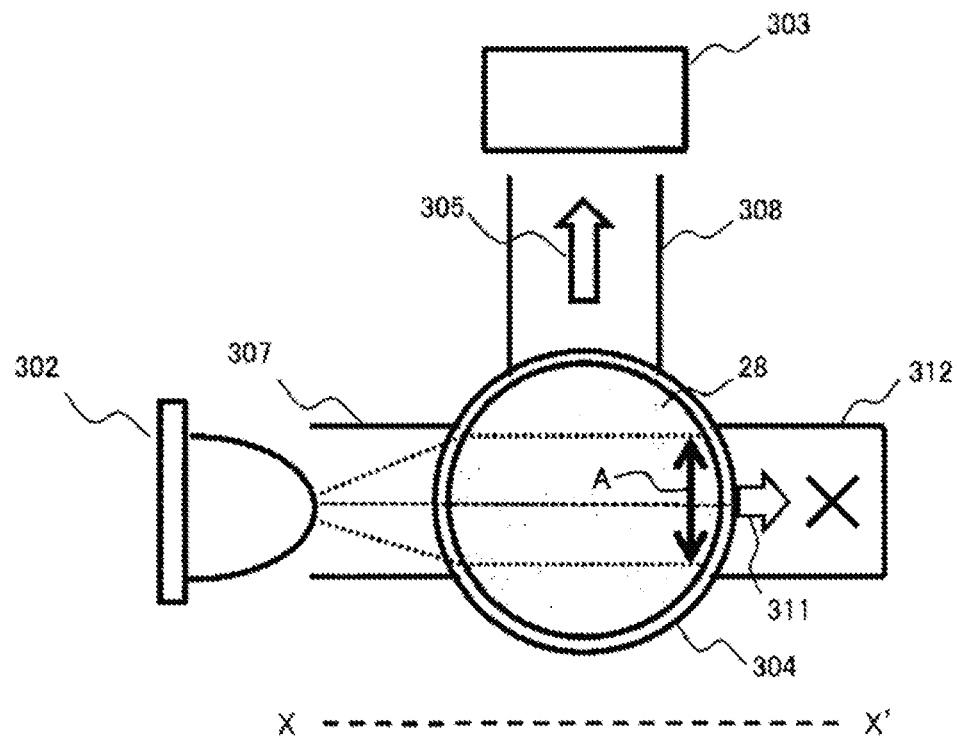
FIGS. 6A and 6B are diagrams (top view) illustrating an optical configuration of the blood coagulation time detecting unit according to the embodiment (Example 7).
Figure 6B:
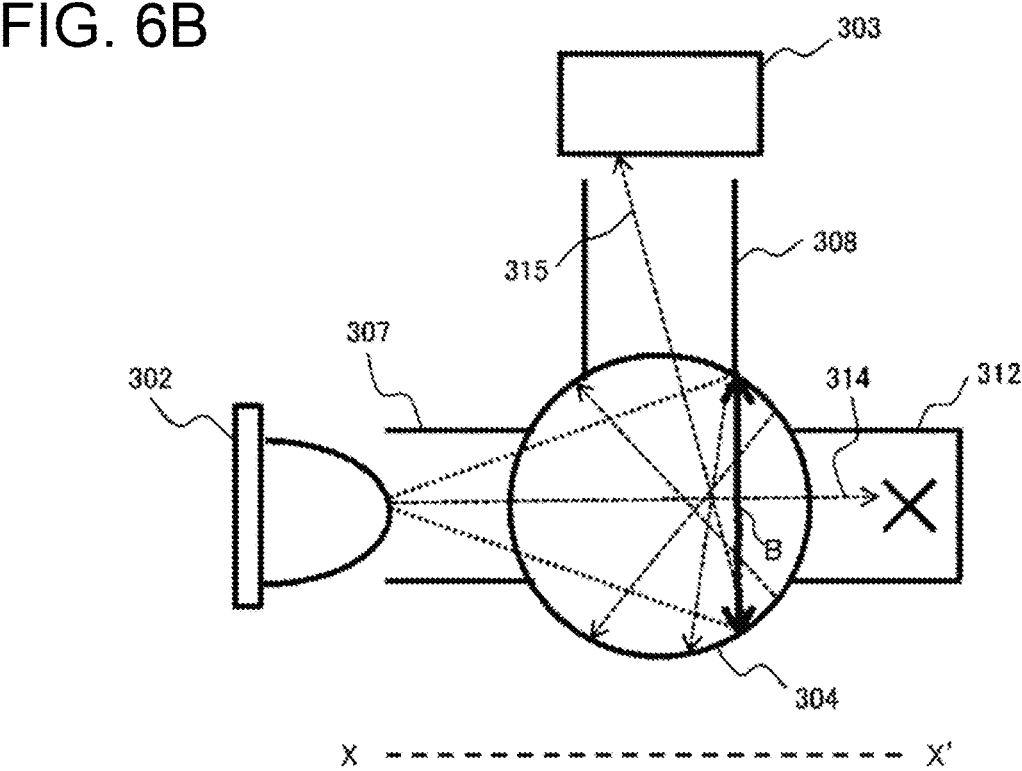

FIG. 6 illustrates an optical configuration (top view) of the blood coagulation time detecting unit according to the embodiment. As illustrated in the drawing, in Example 1, a transmitted light absorbing hole 312 is further provided on a side opposite to the light source 302 of the analysis port 304 (opposite to the light source 302 with respect to the reaction container holding part of the analysis port 304). Here, the transmitted light absorbing hole 312 is arranged at a position where light 314 of the light emitted from the light source 302 reaches which passes the inner wall of the analysis port 304 without colliding with or being reflected thereon in a case where the reaction container (for blood coagulation analysis) 28 is not arranged in the reaction container holding part of the analysis port 304 as illustrated in FIG. 6(b), and the transmitted light absorbing hole 312 is configured such that light 315 of the emitted light that is reflected by colliding with the inner wall of the analysis port 304 enters into the light receiving slit 308 of the scattered light detector 303. Further, the transmitted light absorbing hole 312 is larger than an emission range A of light that is emitted from the light source 302 and transmitted through the reaction container 28 in a case where the reaction container (for blood coagulation analysis) 28 is arranged in the analysis port 304 as illustrated in FIG. 6(a). In addition, the transmitted light absorbing hole 312 is smaller than an emission range B of light that is emitted from the light source 302 in a case where the reaction container (for blood coagulation analysis) 28 is not arranged in the analysis port 304 as illustrated in FIG. 6(b).

As a result, in a case where the reaction container (for blood coagulation analysis) 28 is arranged in the reaction container holding part of the analysis port 304 as illustrated in FIG. 6(a) during the analysis operation, light 311 transmitted through the reaction container (for blood coagulation analysis) 28 enters into the transmitted light absorbing hole 312, is repeatedly reflected and absorbed on the inner surface, and is attenuated. As a result, the amount of light reflected on the reaction container (for blood coagulation analysis) 28 side is reduced, and thus the amount of scattered light to be measured for analysis can be prevented from being inaccurate. Further, in a case where the reaction container (for blood coagulation analysis) 28 is not arranged in the reaction container holding part of the analysis port 304 as illustrated in FIG. 6(b), light that is emitted to the outside of the range of the transmitted light absorbing hole 312 in the light emission range B collides with and is reflected on the inner wall of the analysis port 304. As a result, the generated reflected light 315 is incident on the scattered light detector 303.

Figure 7A:
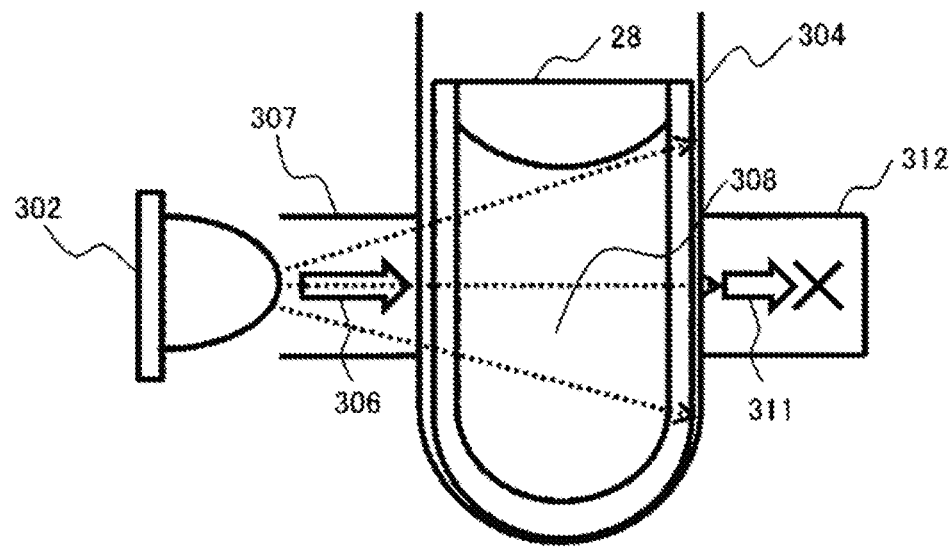
FIGS. 7A and 7B are diagrams (front view) illustrating an optical configuration of the blood coagulation time detecting unit according to the embodiment (Example 7).
Figure 7B:
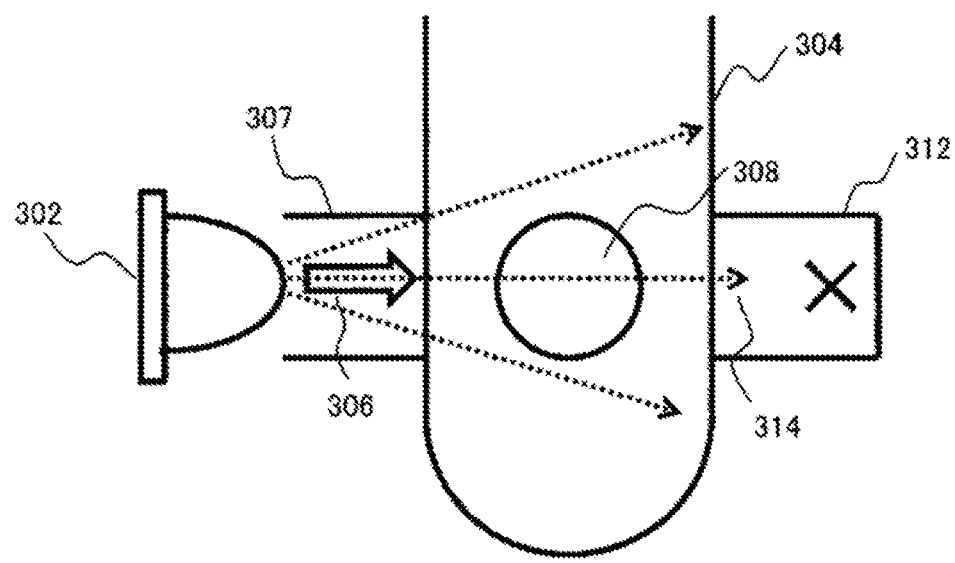

Here, FIG. 7 illustrates an optical configuration of the blood coagulation time detecting unit according to the embodiment (a front view, that is, a cross-sectional view taken along line X-X' of FIG. 6). In a case where the reaction container (for blood coagulation analysis) 28 is arranged in the reaction container holding part of the analysis port 304 as illustrated in FIG. 7(a), when the light emitted from the light source 302 is incident on the reaction container (for blood coagulation analysis) 28 in an up-down direction on the plane of the drawing, refraction is small, and the light is reflected on the wall surface of the analysis port 304 even during the analysis operation. However, due to the arrangement configuration, the light reflected on the wall surface of the analysis port 304 is not incident on the scattered light detector 303 and thus does not affect the analysis result obtained from the detection value of the scattered light detector 303. In addition, a part of the light reflected on the wall surface of the analysis port 304 is scattered in the reaction solution stored in the reaction container (for blood coagulation analysis) 28 such that scattered light is generated. However, due to the arrangement configuration, most of the scattered light is not incident on the scattered light detector 303, and thus the influence thereof on the analysis operation and the analysis result is negligible. That is, the scattered light detector 303 does not substantially detect the light generated by the reflection of the light on the wall surface of the analysis port 304. Therefore, target light that should be detected as the analysis result, that is, light for obtaining a target component in the reaction solution can be accurately and efficiently detected, the reaction solution being the liquid mixture of the sample and the reagent stored in the reaction container (for blood coagulation analysis) 28.

On the other hand, in a case where the reaction container (for blood coagulation analysis) 28 is not arranged in the reaction container holding part of the analysis port 304 as illustrated in FIG. 7(*b*), even when the light emitted from the light source 302 is reflected on the wall surface of the analysis port 304 in the up-down direction on the plane of the drawing, the reflected light is not incident on the scattered light detector 303 due to the arrangement configuration. By providing the transmitted light absorbing hole 312 as in the above-described configuration, the following effects can be obtained. When photometry is performed in order to check the light amount of the light source 302 in a state where the reaction container (for blood coagulation analysis) 28 is not arranged in the reaction container holding part of the analysis port 304, light generated when the light emitted from the light source 302 collides with and is reflected on the analysis port 304 can be detected by the scattered light detector 303. On the other hand, during the analysis operation, the scattered light detector 303 can accurately detect the amount of scattered light required for the analysis of a target component without detecting the reflected light.

Here, in the above-described configuration, the light source 302 may be arranged at a position where the emitted light is parallel in the reaction container (for blood coagulation analysis) 28 when seen from the top of the reaction container (for blood coagulation analysis) 28 as illustrated in FIG. 6(*a*), and the width of the emission slit 307 and the diameter of the transmitted light absorbing hole 312 may be same as each other. That is, assuming that the reaction container (for blood coagulation analysis) 28 corresponds to a lens, by arranging the light source 302 at a focal position, light passing through the inside of the reaction container (for blood coagulation analysis) 28 is parallel.

In this configuration, in a case where the reaction container (for blood coagulation analysis) 28 is not arranged in the reaction container holding part of the analysis port 304, the light emission range can be more reliably set to be larger than the transmitted light absorbing hole 312. In addition, in a case where the reaction container (for blood coagulation analysis) 28 storing the reaction solution is arranged in the reaction container holding part of the analysis port 304, the light emission range can be set to be smaller than the transmitted light absorbing hole 312. Therefore, the light amount check operation can be reliably performed while reducing the influence of the reflected light on analysis during the analysis operation.

Example 8

In Examples 1, 6, and 7, by feedbacking the light amount check result of the light source 302 using the computer 105, a driving current applied to the light source 302 may be controlled and the light amount may be automatically adjusted such that the amount of emitted light is constant all the time.

According to the embodiment, deterioration of the light source 302 or incorporation of foreign matter into an optical path can be detected, and the amount of emitted light can be adjusted to be constant all the time such that the analysis result can be more stably obtained. In addition, time and effort for adjusting the light amount during product shipping or replacement of the light source 302 can be reduced.

Example 9

FIG. 8 is a diagram illustrating an optical configuration (top view) of the blood coagulation time detecting unit according to the embodiment. In Examples 1, 6, and 7, as illustrated in the drawing, in a region (first region) of the inner wall surface of the reaction container holding part of the analysis port 304 that is opposite to the scattered light detector 303, a reflectance may be intentionally increased by masking or cutting. It is desirable that, only in a case where the reaction container (for blood coagulation analysis) 28 is not arranged in the analysis port 304, the region that is treated to increase the reflectance is a surface that becomes a range 316 that is in the emission range of the light source 302 and where light reflected by colliding the region reaches the scattered light detector 303. In addition, a region (second region) of the inner wall surface of the analysis port 304 other than the first region may be coated or surface-treated such that the reflectance decreases.

Here, as the treatment for increasing the reflectance, the range 306 may be coated or surface-treated to slightly reflect the emitted light, and the region of the inner wall surface of the analysis port 304 other than the range 306 may be coated or surface-treated such that the reflectance decreases.

With this configuration, it is possible to secure the amount of reflected light required for the light amount check operation of the light source 302 in a case where the reaction container (for blood coagulation analysis) 28 is not arranged in the analysis port 304, and to minimize reflection of emitted light or scattered light during the analysis operation where the reaction container (for blood coagulation analysis) is arranged in the analysis port 304. As a result, the analysis performance can be improved and stabilized.

Example 10

Figure 9A:
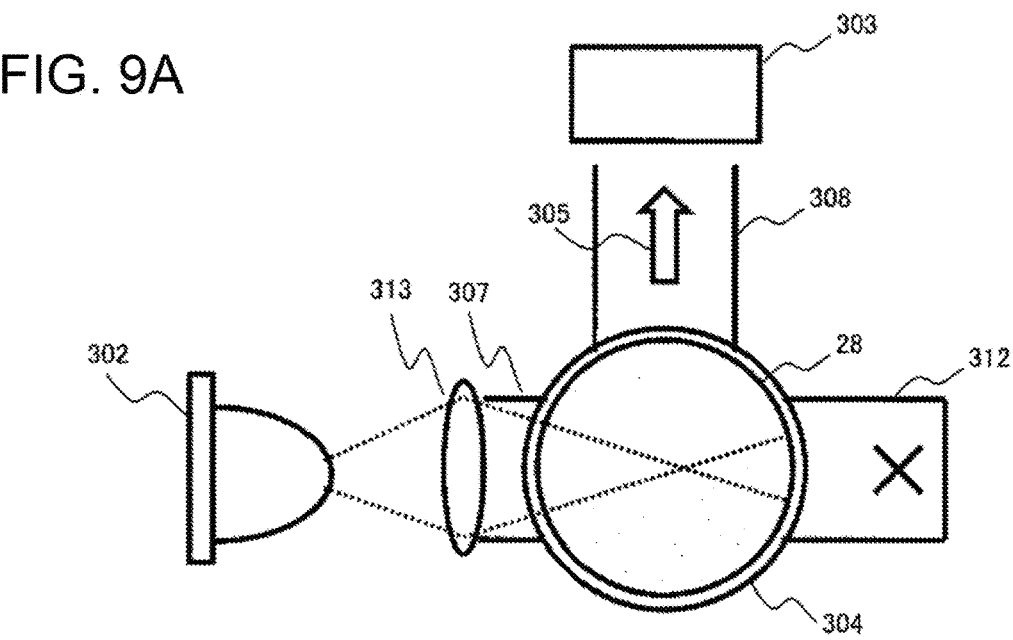
FIGS. 9A and 9B are diagrams (top view) illustrating an optical configuration of the blood coagulation time detecting unit according to the embodiment (Example 10).
Figure 9B:
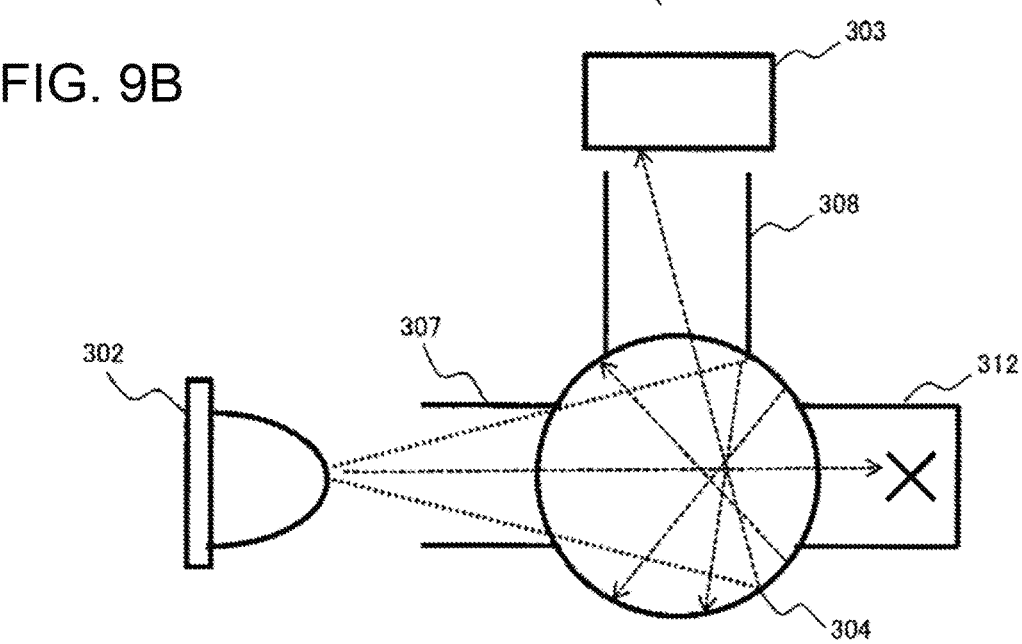

FIG. 9 is a diagram illustrating an optical configuration (top view) of the blood coagulation time detecting unit according to the embodiment. In Examples 1, 6, and 7, as illustrated in the drawing, a lens 313 that collects the emitted light and is designed to prevent the emitted light to collide with the wall surface of the analysis port 304 may be provided between the light source 302 and the reaction container (for blood coagulation analysis) 28 in a state where the reaction container (for blood coagulation analysis) 28 is arranged in the analysis port 304, and a moving mechanism of the lens 313 may be provided such that the lens 313 is inserted to be positioned on the optical path of the light emitted from the light source 302 during the analysis operation where the reaction container (for blood coagulation analysis) 28 is arranged as illustrated in FIG. 9(*a*) and such that the lens 313 is retracted from the optical path of the light emitted from the light source 302 during the light amount check operation where the reaction container (for blood coagulation analysis) 28 is not arranged as illustrated in FIG. 9(*b*).

In this configuration, during the analysis operation, the light emitted from the light source 302 does not spread in the up-down direction on the plane of the drawing due to the effect of the lens 313. Therefore, the amount of scattered light can be more accurately obtained than in Examples. In addition, during the light amount check operation, by retracting the lens from the optical path of the light emitted from the light source 302, the emitted light collides with and is reflected on the inner wall surface of the analysis port 304. As a result, by detecting the reflected light, the light amount of the light source 302 can be checked.

REFERENCE SIGNS LIST

1: automatic analysis apparatus
2: blood coagulation time analyzing unit
11: sample disk
12: sample dispensing probe
13: reaction disk
14: second reagent dispensing probe
15: first reagent disk
16: second reagent disk
17: first reagent dispensing probe
18: sample dispensing position
19: photometer
20: blood coagulation reagent dispensing probe
21: blood coagulation time detecting unit
23: reaction container transport mechanism
24: reaction container disposal hole
25: reaction container magazine
26: reaction container (for biochemical analysis)
27: sample container
28: reaction container (for blood coagulation analysis)
101: interface
102: external output medium
103: display device
104: memory
105: computer
106: printer
107: input device
201: sample dispensing control unit
202: transport mechanism control unit
203: A/D converter (2)
204: blood coagulation reagent dispensing control unit
205: A/D converter (1)
206: reagent dispensing control unit (1)
207: reagent dispensing control unit (2)
302: light source
303: scattered light detector
304: analysis port
305: scattered light
306: emitted light
307: emission slit
308: light receiving slit
309: transmitted light detector
310: transmitted light slit
311: transmitted light
312: transmitted light absorbing hole
313: lens
314: light emitted from light source (in case where reaction container is not arranged)
315: light that collides with and reflected on inner wall of analysis port (in case where reaction container is not arranged)
316: range that is treated to increase reflectance

The invention claimed is:

1. An automatic analysis apparatus comprising:
an analysis port including a reaction container holding part that holds a reaction container storing a liquid mixture of a sample and a reagent, a light source that emits light to the liquid mixture stored in the reaction container held by the reaction container holding part, and a detector that detects light generated when the light is emitted from the light source to the liquid mixture as generated light; and
a control unit that controls the analysis port, wherein
the sample is analyzed based on information on the detected generated light,
a surface of the reaction container holding part is configured to reflect at least a part of the light emitted from the light source, and
the control unit executes control so as to emit the light from the light source in a state where the reaction container is not held by the reaction container holding part, to detect the light reflected on the surface of the reaction container holding part by the detector as reflected light, and not to use the analysis port for analysis when a result of a detection of the reflected light shows that the detected reflected light is less than a first value determined in advance.

2. The automatic analysis apparatus according to claim 1, further comprising:
a storage unit that stores information relating to an intensity of the detected generated light, a cumulative operating time of the light source at the time of the detection of the detected generated light, and a date and time when the detection of the detected generated light is performed in the result of the detection of the detected generated light; and
a display unit that displays the result of the detection of the detected generated light in a chronological manner based on the stored information.

3. The automatic analysis apparatus according to claim 1, further comprising:
a storage unit that stores information relating to an intensity of the detected generated light, a cumulative operating time of the light source at the time of the detection of the detected generated light, and a date and time when the detection of the detected generated light is performed in the result of the detection of the detected generated light; and
a display unit, wherein
the control unit estimates a period during which the intensity of the detected generated light is less than the first value based on the stored information and displays a display urging replacement of the light source during the estimated period on the display unit.

4. The automatic analysis apparatus according to claim 1, wherein
the detector is a first detector that detects scattered light generated when light is emitted from the light source to the liquid mixture stored in the reaction container,
the automatic analysis apparatus further comprises a second detector that detects transmitted light when light is emitted from the light source to the liquid mixture stored in the reaction container, and
the control unit analyzes a sample based on information on the light detected by any one of the first detector or the second detector.

5. The automatic analysis apparatus according to claim 1, wherein
the control unit controls a driving current of the light source based on a result of a detection of the generated light such that the intensity of the light emitted from the light source is constant.

6. The automatic analysis apparatus according to claim 1, wherein
a first region of the surface of the inner wall of the reaction container holding part is configured such that a reflectance of the light emitted from the light source in the first region is higher than that in a second region other than the first region, and the first region is in an emission range of the light emitted from the light source in a state where the reaction container is not held by the reaction container holding part and is configured such that light reflected by colliding with the first region reaches the detector.

7. The automatic analysis apparatus according to claim 6, wherein the second region is configured such that the reflectance of the light emitted from the light source decreases.

8. The automatic analysis apparatus according to claim 1, wherein the control unit executes control so as to emit light from the light source in a state where the reaction container is not held by the reaction container holding part to intermittently detect light reflected on a surface of an inner wall of the reaction container holding part by the detector after the emission of the light as reflected light, to determine whether or not an intensity of the light source is stable based on the result of the detection of the reflected light, and to allow execution of an operation after the result of the detection of the reflected light shows that the intensity of the light source is stable.

9. The automatic analysis apparatus according to claim 8, wherein the control unit displays a result of a determination showing that the intensity of the light source is stable on a display unit.

10. The automatic analysis apparatus according claim 1, further comprising:

a storage unit that stores information relating to an intensity of the detected generated light and a date and time when the detection of the detected generated light is performed in the result of the detection of the detected generated light, wherein the control unit executes control so as to compare the intensity of the detected generated light in the result of the detection of the detected generated light to an intensity of previously detected light stored in the storage unit and not to use the analysis port for analysis when a result of a comparison shows that the intensity of the detected generated light and the intensity of the previously detected light are different from each other by more than a predetermined range.

11. The automatic analysis apparatus according to claim 10, wherein the control unit displays a display urging maintenance of the apparatus on a display unit when the result of the comparison shows that the intensity of the detected generated light and the intensity of the previously detected light are different from each other by more than the predetermined range.

12. The automatic analysis apparatus according to claim 1, wherein the control unit executes control so as not to use the analysis port for analysis when the result of the detection shows that the detected reflected light is more than the first value and more than a second value determined in advance.

13. The automatic analysis apparatus according to claim 12, wherein the control unit issues an alarm when the result of the detection shows that the detected reflected light is less than the first value or more than the second value.

14. The automatic analysis apparatus according to claim 12, further comprising:

a setting unit that is capable of setting a timing at which the control unit executes control so as not to use the analysis port for analysis when the result of the detection shows that the detected reflected light is less than the first value or more than the second value.

15. The automatic analysis apparatus according to claim 14, wherein the timing includes at least one of a timing at which the apparatus starts, a timing at which an operation starts, and a timing at which a maintenance starts.

16. The automatic analysis apparatus according to claim 1, wherein the analysis port includes a hole portion that absorbs the light emitted from the light source on a side opposite to the light source with respect to the reaction container, and the hole portion is larger than a range of light emitted from the light source and transmitted through the reaction container in a state where the reaction container is held by the reaction container holding part and is smaller than an emission range of the light emitted from the light source in a state where the reaction container is not held by the reaction container holding part.

17. The automatic analysis apparatus according to claim 16, wherein the light source is arranged such that the light emitted from the light source is parallel in the reaction container.

18. The automatic analysis apparatus according to claim 16, further comprising an emission slit that adjusts the range of the light emitted from the light source, wherein a diameter of the hole portion is same as a width of the emission slit.

19. The automatic analysis apparatus according to claim 16, further comprising a lens that is movable between the light source and the reaction container holding part on an optical path of the light emitted from the light source, wherein the control unit controls the lens to be positioned on the optical path in a state where the reaction container is held by the reaction container holding part and to be retracted from the optical path in a state where the reaction container is not held by the reaction container holding part.

20. An analysis method using an automatic analysis apparatus including an analysis port including a reaction container holding part that holds a reaction container storing a liquid mixture of a sample and a reagent, a light source that emits light to the liquid mixture stored in the reaction container held by the reaction container holding part, and a detector that detects light generated when the light is emitted from the light source to the liquid mixture, and a control unit that controls the analysis port, the method comprising:

analyzing the sample based on information on the detected light, reflecting at least a part of the light emitted from the light source by a surface of an inner wall of the reaction container holding part, and controlling the automatic analysis apparatus so as to emit the light from the light source in a state where the reaction container is not held by the reaction container holding part, to detect the light reflected on the surface of the inner wall of the reaction container holding part by the detector as reflected light, and not to use the analysis port for analysis when a result of a detection of the reflected light shows that the detected reflected light is less than a first value determined in advance.

* * * * *